United States Patent
Szekeres et al.

(10) Patent No.: US 7,326,560 B2
(45) Date of Patent: Feb. 5, 2008

(54) TISSUE MICRO-ARRAY BUILDER MANUAL TEST

(76) Inventors: György Szekeres, Akác u. 8., H-7632 Pécs (HU); Zsuzsanna Halas, Mária u. 16., H-7621 Pécs (HU); Lászlóné Zorn, Uitz B. u. 17., H-7632 Pécs (HU)

( * ) Notice: Subject to any disclaimer, the term of this patent is extended or adjusted under 35 U.S.C. 154(b) by 560 days.

(21) Appl. No.: 10/520,003

(22) PCT Filed: Jun. 17, 2003

(86) PCT No.: PCT/HU03/00044

§ 371 (c)(1),
(2), (4) Date: Dec. 27, 2004

(87) PCT Pub. No.: WO04/000992

PCT Pub. Date: Dec. 31, 2003

(65) Prior Publication Data

US 2005/0260740 A1    Nov. 24, 2005

(30) Foreign Application Priority Data

Jun. 25, 2002   (HU) ................................. 0200185 U

(51) Int. Cl.
*C12M 1/00*     (2006.01)
*C12M 3/00*     (2006.01)
(52) U.S. Cl. .................... 435/283.1; 435/307.1
(58) Field of Classification Search ............ 435/283.1, 435/307.1
See application file for complete search history.

(56) References Cited

U.S. PATENT DOCUMENTS

| | | | |
|---|---|---|---|
| 4,820,504 A | 4/1989 | Battifore | 435/7.23 |
| 5,002,377 A | 3/1991 | Battifore et al. | 359/398 |
| 6,103,518 A | 8/2000 | Leighton | 435/286.3 |
| 6,383,801 B1 | 5/2002 | Leighton | 359/398 |
| 6,468,783 B1 * | 10/2002 | Leighton | 435/286.3 |
| 7,029,615 B2 * | 4/2006 | Lilischkis et al. | 264/248 |

FOREIGN PATENT DOCUMENTS

| | | |
|---|---|---|
| WO | WO 01/44063 | 9/1999 |
| WO | WO 01/22086 | 3/2001 |
| WO | WO 01/42796 | 6/2001 |
| WO | WO 01/51910 | 7/2001 |
| WO | WO 01/98525 | 12/2001 |
| WO | WO 03/044213 | 5/2003 |

* cited by examiner

*Primary Examiner*—Walter D. Griffin
*Assistant Examiner*—Shanta G Doe
(74) *Attorney, Agent, or Firm*—Joseph G. Seeber

(57) ABSTRACT

The tissue micro-array (TMA) building manual set, which includes a well-known SZK tissue core punch extractor and a TMA block mould (1) characterized as follows: the TMA block mould (1) consists of a lower (2) and an upper (3) part, the lower part (2) is equipped with mandrels (4) at right angles to the base unit arranged in the middle into lines and columns, the upper part (3) has a margin-containing (7) cleavage (6), which receives the mandrels (4) when the TMA block mould (1) is assembled, the margin (7) and size of the cleavage (6) fit to the shape and size of the paraffin block holder (PBK), and the lower (2) and upper (3) parts are connected to each other with directing nipples (5) and threaded arms (9) fixed horizontally.

4 Claims, 3 Drawing Sheets

TISSUE MICRO-ARRAY BUILDER MANUAL TEST

TECHNICAL FIELD

The invention generally relates to a tissue micro-array (TMA) building manual set, which includes a tissue core punch extractor and a TMA block mould with lower and upper parts.

The tissue micro-array building manual set is suitable for making TMA series, which enables the fast and accurate "home-made" preparation of TMA series well-fitted to the traditional, routine histology laboratory conditions.

BACKGROUND ART

TMA technology can be applied for the determination of diagnostic markers, as well as parameters related to the aggressiveness and other features of malignant tumors.

TMA is very useful for retrospective studies, i.e., for the investigation of thousands of molecular biological markers in thousands of histological specimens stored in pathology laboratories.

Similar to the DNA-chip, which allows the analysis of the genome mutations and abnormal gene expressions, the tissue micro-arrays enable the parallel processing of biological specimens. By using only one TMA, researchers have the opportunity for simultaneous comparative examination of various molecular parameters (DNA, RNA molecular biological techniques and immunohistochemistry/immunocytochemistry of antigens) in histological specimens of several malignant tumor tissues.

Numerous monoclonal antibodies, which determine the genome and phenotype of intact and pathological (mainly malignant) cells, and which are specific for novel antigen-determinants, are being developed and introduced for diagnostic and therapeutic applications (immunomorphology). Diagnostic measures based on genetic methods, which can identify certain segments of DNA and/or RNA, are increasingly used (molecular biology). Several laboratories are involved in evaluating their tissue reactivity and potential applicability in the most prevalent tumors.

As a consequence, this diagnostic technique indeed seems to be widely used.

In the diagnostic technique, histology specimens from different tumor tissues are embedded in properly arranged sets into paraffin for the preparation of TMA. The TMA block is cut giving the various tumor tissues as point-like items in the histological light microscopic sections. Since each TMA block may render hundreds of parallel, 34 micrometers thick serial sections, hundreds of molecular parameters can be examined on the same micro-array. Several tumor markers can be analyzed within weeks, while this would take months per tissue specimen using the traditional method.

According to our current knowledge, reactions made on standard-size histological sections (from frozen and/or fixed-embedded tissues) and cytological samples (smears, sediments, imprints, cytocentrifugates, etc) are useful for the identification of molecular markers of tumors and for the prediction of disease progression. At the same time, only a limited number of samples can be examined due to technical and financial reasons, the evaluation is time-consuming and comparative, and reproducible examinations among different laboratories are difficult to carry out. First of all, die lack of reproducibility is the disadvantage of the so-called "multi-tissue block" technique that contains parts from various tissues/blocks in a simple histological block. Moreover, the distribution of individual molecular markers within the malignant tissue is often quite heterogeneous and, thus, a minute tissue part does not properly represent the biological features of the entire tumor cell population.

Application of the technique reminiscent of or based on the "chip" technology, i.e. the tissue micro-arrays, enables the investigation of hundreds or thousands of tissue specimens.

The knowledge in the field of medical biotechnological basic research is being multiplied, and its employment confirms both diagnostic and therapeutic measures. Nevertheless, the related applied research, research and development (R&D), and clinical testing processes require years or even a decade and proportional financial means. In accordance with our invention, the TMA building manual set shortens the necessary testing phase in an accurate and cost-efficient way.

The information in U.S. Pat. No. 4,820,504 represents a well-known and widely used procedure, which serves for the preparation of a sample containing multiple tissue specimens. Its advantages include the simple procedure that can be applied in almost every laboratory equipped with routine and research facilities, low costs, and no need for procurement of new devices. However, the disadvantage of the technique is that the consecutive, side by side embedded tissue samples are randomly situated, not organized into lines and columns, which makes the evaluation rather difficult, and the automatic (image analyzing) processing almost impossible or complicated and slow. In addition, the size of the individual tissue samples are merely roughly similar to each other. A new instrument is not set forth in the description of die procedure.

Our procedure and our invention are aimed at addressing these disadvantages.

U.S. Pat. No. 5,002,377 discloses an instrument which organizes tissue samples into regular lines and columns, and so gives a multiple tissue block. Its patent holder is the same as that of the previous instrument who is a well-known expert in this field, although this technique has not become widely used. Its obvious advantage is that application of this instrument enables the preparation and embedding of regular, almost identical size tissue samples. Nevertheless, its disadvantage lies in the fact that the individual tissue columns may be, though only slightly, shifted during block preparation. The largest disadvantages of the instrument are its incompatibility with the most frequently applied and best known laboratory instruments (devices and semi-fixed assets) and, on the other hand, the need for three additional tools and the significant manual skills for their application. The first instrument includes multiple parallel cutting plates, which can cut out tissue columns from tissue samples, but which can be applied exclusively on larger specimens. The other two components make possible the embedding of cut tissue columns into a single paraffin block.

U.S. Pat. No. 6,103,518 discloses a table device giving useful tissue micro-arrays. The procedure is based on the well-oriented technique of the recipient places of the paraffin block and the sampling from the selected sites of donor blocks (tissue cores). Besides its aforementioned advantages, its high price, complicated mechanical settings, and the need for one-by-one preparation of recipient holes of the recipient block represent serious drawbacks in the daily practice.

PCT Publication No. WO 01/51910 presents a simple paraffin block construction procedure that can be used for the production of tissue micro-array series in which a mould that consists of several elements has been formed. On using the mould, a basic body is moulded that has regularly arranged openings into which the issue samples are then placed. Following this, the basic body containing the tissue samples is heated up to the softening temperature limit in the interest of the basic body being able to combine with the liquid paraffin poured onto one of the surfaces in the following phase of the procedure and so form a single unit with it. This liquid paraffin layer serves to assist in the fixing of the paraffin block holder to the paraffin block containing the cylindrical holes and the tissue samples contained in them.

However, a significant disadvantage of this solution is that the paraffin block that contains the cylinders with the tissue samples in them is subjected to a significant heat effect. Due to the heat effect and the re-softening of the paraffin, the tissue cylinders move, which can cause problems when making the sections. Another disadvantage of the subsequent heat effect is that the amount of heat required to soften the paraffin may damage the tissue sample cylinders, which may cause irreversible damage from the point of view of the immune staining, as this results in a change to the protein-based antigens, and this can lead to the sample being unusable.

Another significant disadvantage of the solution is that, in the paraffin block poured in two phases, due to the shear forces occurring when producing the section, the paraffin block may come apart at the border between the two layers made at two separate points in time, as a result of which the paraffin block may separate from the block holder, making it impossible to make the desired sections from the tissue cylinders.

Examples suitable for the production of paraffin blocks used for the production of tissue samples can also be found in U.S. Pat. No. 6,383,801 and, furthermore, in PCT Publication Nos. WO 01/98525, WO 99/44063, WO 01/220861 and WO 01/42796.

DISCLOSURE OF INVENTION

The objective of our invention is to eliminate the disadvantages of the above mentioned methods and to design a tissue micro-array building manual set that is simple, cheap, and compatible with all widely used histological laboratory fixed and semi-fixed assets. The principle of applying the manual apparatus is that the preparation of the recipient block is separated from the sampling. Therefore, the samples can be previously prepared and stored elsewhere, then put into the recipient block. The manual apparatus requires small space and is easy to clean, there is basically no need for maintenance, each pan is resistant to external physical and chemical impacts, and the recipient block can be prepared in one step.

Our invention is based on the recognition that the tissue micro-array building manual set should be made from elements which fit together in their size, and which can be applied along with the instruments used under the traditional routine histological laboratory conditions. This tissue micro-array preparing manual apparatus set was developed to contain a tissue core punch extractor and a TMA block mould with lower and upper parts, and the traditional, most frequently used paraffin block holders fit well with this latter one. The tissue core punch extractor is a well-known technical solution, i.e., its function is based on punching. The punching tip is made as a punching rube with an internal diameter of 1 or 2 mm. This punching tube receives the tissue cylinder (core) taken from a given place of the sample (donor block), which can be manually pushed out from the punching tip by help of a piston-like needle probe pushed back by a coil spring inside the instrument. The external diameter of the needle probe is comparable to the internal diameter of the punching tip, but due to its size it can freely slide within the punching tip.

The TMA block mould is made up of two main elements: the lower and upper parts. The lower part is equipped with 1 or 2 mm wide, mandrels, identical with the diameter of the punching tube, organized into lines and columns. Since the lower and upper parts are assembled together during the casting of the paraffin block and the paraffin is poured into the hole formed by the upper part, a margin should have been prepared there, which margin is identical in its size and shape to the size and shape of the generally used paraffin block holder.

The formation of the margin creates the opportunity to fix the paraffin block holder itself to the empty paraffin block in one step when moulding the paraffin block. This, later on, makes it unnecessary to carry out the subsequent heat treatment, which is essential in the known procedures, and thus overcomes the disadvantageous consequences presented above and deriving from heat treatment.

At the lower part, at least two vertical directing nipples are built into the base unit, which ensures the parallel and intact removal of the paraffin block when the mould manual apparatus is taken apart. The equal withdrawal of the two elements at the opening of the lower and upper pan of the TMA block mould is ensured by at least two diagonally arranged threaded arms.

The elimination of the above discussed disadvantages is ensured by a tissue micro-array building manual set with the following characteristics: a tissue core punch extractor and a TMA block mould, the latter having a lower and upper part; the lower part is organized in the middle into lines and columns, set up with mandrels at right angles to the base unit; the upper part is prepared with a margin-containing cleavage, which receives the mandrels when the TMA block mould is assembled together; the margin and size of the cleavage fit the shape and size of the paraffin block holder; the lower and upper parts are connected to each other with directing nipples and threaded arms fixed horizontally; the lower pan of the TMA block mould has at least two vertical directing nipples, which vertically and detachably join into the bore-holes of the upper part; and, in the upper part of the TMA block mould, there are at least two diagonal transit bore-holes, which receive the threaded arms, and the endings of the threaded arms sit on the lower part when the TMA block mould is assembled together.

BRIEF DESCRIPTION OF DRAWINGS

Our inventions the TMA building manual set, is presented in detail by means of the following drawings.

DETAILED DESCRIPTION

Figure 1:
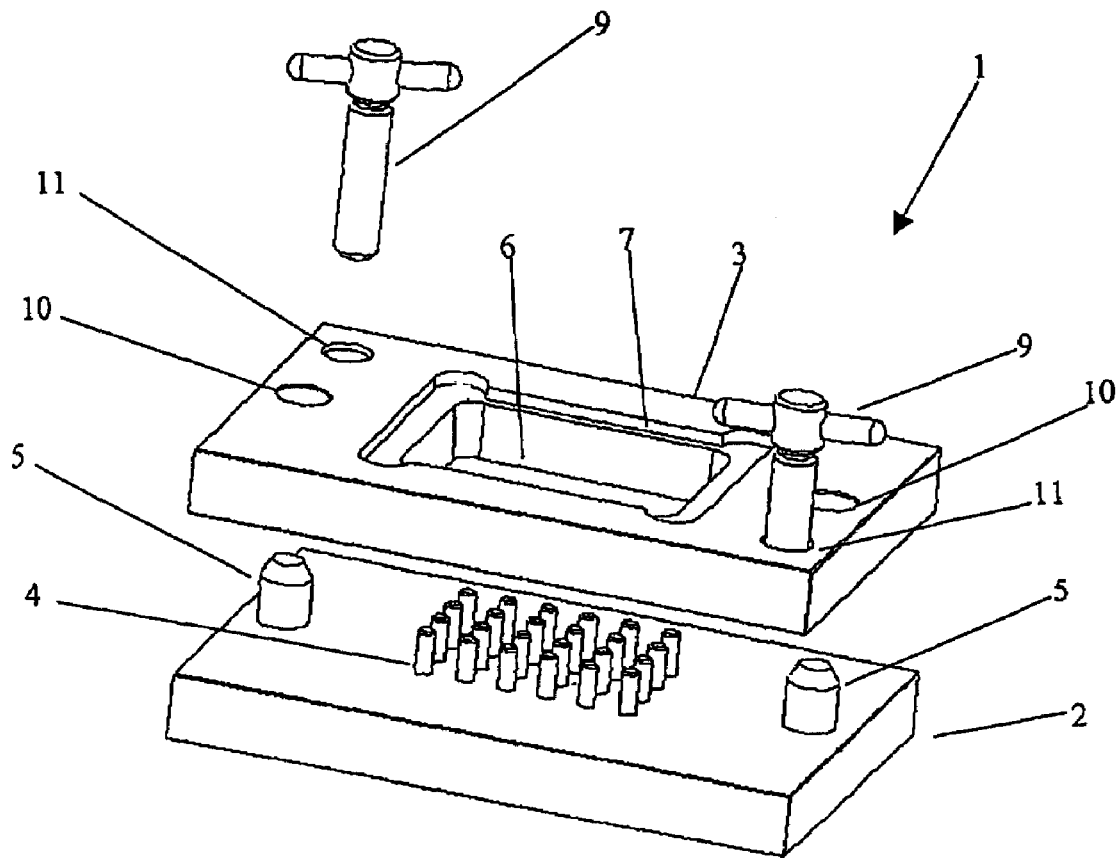
FIG. 1 depicts an axonometric delineation of the TMA block mould.
Figure 2:
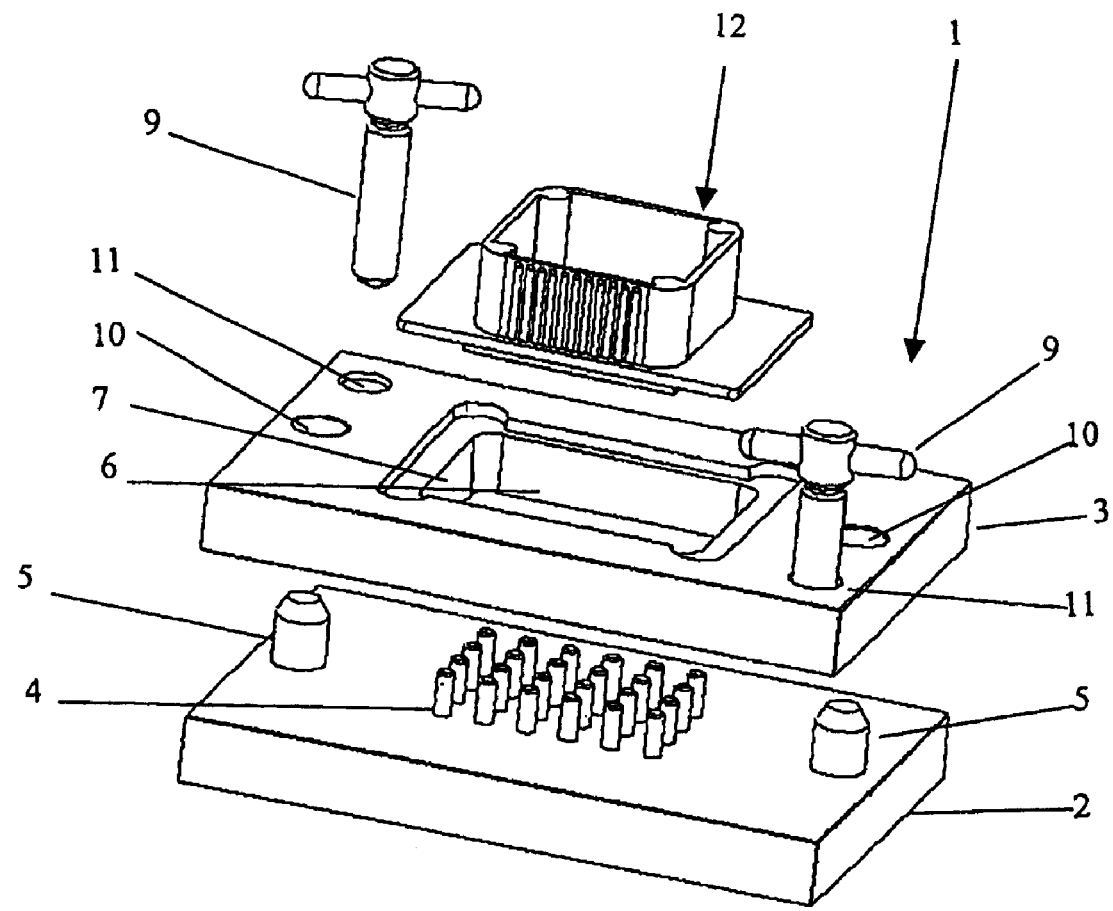
FIG. 2 depicts an axonometric delineation of the TMA block mould and paraffin block holder of the TMA building manual set.
Figure 3:
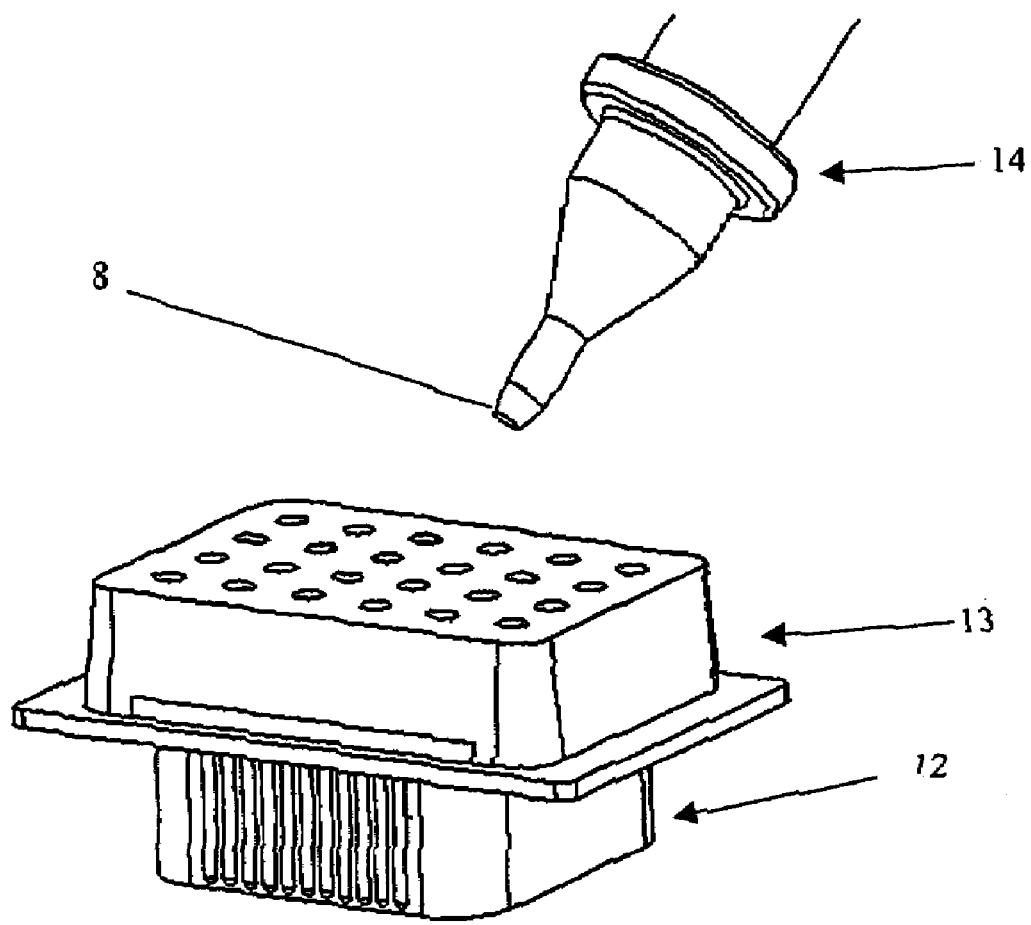
FIG. 3 depicts a finished paraffin block with the tissue core punch extractor.

The TMA block mould 1 shown in FIG. 1 is made up of two major elements, i.e., lower part 2 and upper part 3. The lower part 2 has mandrels 4 with 1 or 2 mm diameter arranged into lines and columns. The diameter of the mandrel 4 is identical to the diameter of the punching tube 8 of the tissue core punch extractor 14. On the lower part 2, there are directing nipples 5 at right angles to the lower part 2, which ensure the parallel and intact removal of the paraffin block when the TMA block mould 1 is dismantled. The size of the upper part 3 is identical to that of the lower part 2 and, in the middle, it has a cleavage 6 containing a margin 7, which receives the mandrels 4. The margin 7 of the cleavage 6 is made to receive the commercially available paraffin block holder 12 shown in FIG. 2. On the lower part 2, there are directing nipples 5 which join the transit bore-holes 10 on the upper part 3. Moreover, the additional transit bore-holes 11 on the upper part 3 receive the threaded arms 9, which ensure the even and parallel opening of the two parts of the assembled instrument cast with paraffin block.

The equal withdrawal of the two elements at the opening of the lower part 2 and upper part 3 of the TMA block mould 1 is ensured by at least two diagonally arranged threaded arms 9. The tissue core punch extractor 14 ends in a punching tube 8 with an internal diameter of 1 or 2 mm.

The well-known tissue core punch extractor 14 receives the tissue cylinder taken from a given place of the sample (donor block), which can be manually pushed out from the punching tube 8 by means of a piston-like needle probe (not shown) pushed back by a coil spring (not shown) inside the instrument.

The external diameter of the needle robe is comparable to the internal diameter of the punching tube 8, but due to its size, it can freely slide within the punching tube 8.

On preparing the paraffin block, the assembled TMA block mould 1 is filled with paraffin through the cleavage 6. After the paraffin is set when cooled down and removed from the instrument, it gives a paraffin block (recipient block) 13 containing 1 or 2 mm wide cylindrical holes with parallel longitudinal axes organized into regular lines and columns. These holes receive the tissue cores having the same diameter taken out of the donor blocks by the tissue core punch extractor 14, giving finally the TMA block.

As can be seen from the above description, our objective was accomplished by the development of our invention. The TMA building manual set is a simple, cheap manual instrument, which is easy to handle and clean, environment-friendly, and enables the fast and accurate preparation of TMA under the traditional, routine histological laboratory conditions.

A further advantage is that, due to the unique formation of the manual set, it is possible to produce the paraffin block with a holder in one step without any subsequent heat treatment, which not only reduces the time required for production, but also has a favourable effect on the mechanical characteristics of the finished piece, that is, also including shearing strength.

The invention claimed is:

1. A tissue micro-array (TMA) builder manual set, comprising:
   a tissue core punch extractor;
   a TMA block mold which includes a lower part and an upper part;
   a paraffin block holder;
   wherein said lower part of said TMA block mold includes mandrels disposed vertically and arranged in rows and columns;
   wherein said upper part of said TMA block mold includes a cleavage surrounded by a margin for receiving said mandrels when said TMA block mold is assembled;
   wherein said margin and a size of said cleavage are such as to fit a shape and a size of said paraffin block holder; and
   wherein said TMA builder manual set further comprises direct nipples and threaded arms for connecting said lower and upper parts of said TMA block mold.

2. The TMA builder manual set of claim 1, wherein said lower part of said TMA block mold further includes at least two vertically directed nipples, and said upper past of said TMA block mold has bore holes formed therein, and wherein said at least two vertically directed nipples are arranged in a vertical direction and join said bore holes.

3. The TMA builder manual set of claim 2, wherein said lower part of said TMA block mold further includes threaded arms, and said upper part of said TMA block mold has at least two additional bore holes formed therein for receiving said threaded arms of said lower part of said TMA block mold when said TMA block mold is assembled.

4. The TMA builder manual set of claim 1, wherein said lower part of said TMA block mold further includes threaded arms, and said upper part of said TMA block mold has at least two additional bore holes formed therein for receiving said threaded arms of said lower part of said TMA block mold when said TMA block mold is assembled.

* * * * *